United States Patent
Housman et al.

(10) Patent No.: US 10,631,850 B2
(45) Date of Patent: Apr. 28, 2020

(54) AXIALLY-COMPLAINT DRIVER ASSEMBLY

(71) Applicants: Smith & Nephew, Inc., Memphis, TN (US); Smith & Nephew Orthopaedics AG, Baar (CH); Smith & Nephew Pte. Limited, Singapore (SG)

(72) Inventors: Mark Edwin Housman, North Attleborough, MA (US); Robert B. Litchfield, London (CA); Scott W. Trenhaile, Belvidere, IL (US); Marc Joseph Balboa, Hopkinton, MA (US)

(73) Assignees: Smith & Nephew, Inc., Memphis, TN (US); Smith & Nephew Orthopaedics AG (CH); Smith & Nephew Pte. Limited, Singapore (SG)

( * ) Notice: Subject to any disclaimer, the term of this patent is extended or adjusted under 35 U.S.C. 154(b) by 225 days.

(21) Appl. No.: 15/987,040

(22) Filed: May 23, 2018

(65) Prior Publication Data

US 2019/0357898 A1  Nov. 28, 2019

(51) Int. Cl.
*A61B 17/04* (2006.01)
*A61F 2/08* (2006.01)
*A61B 90/00* (2016.01)
*A61B 17/00* (2006.01)

(52) U.S. Cl.
CPC ........ *A61B 17/0401* (2013.01); *A61F 2/0811* (2013.01); *A61B 2017/0042* (2013.01); *A61B 2017/00367* (2013.01); *A61B 2017/00862* (2013.01); *A61B 2017/00991* (2013.01); *A61B 2017/0409* (2013.01); *A61B 2090/034* (2016.02); *A61F 2002/0852* (2013.01)

(58) Field of Classification Search
CPC ...... A61B 17/0401; A61B 2017/00991; A61B 2017/0409; A61F 2/0811; A61F 2002/0852; B25B 13/466; B25B 19/00
See application file for complete search history.

(56) References Cited

U.S. PATENT DOCUMENTS

| | | | |
|---|---|---|---|
| 2008/0058816 A1* | 3/2008 | Philippon | A61B 17/0401 606/326 |
| 2010/0130989 A1* | 5/2010 | Bourque | A61B 17/0483 606/144 |
| 2014/0277129 A1* | 9/2014 | Arai | A61B 17/0401 606/232 |

* cited by examiner

*Primary Examiner* — Tuan V Nguyen
(74) *Attorney, Agent, or Firm* — Burns & Levinson, LLP; Joseph M. Maraia; Marlo Schepper Grolnic (57) ABSTRACT

Driver assemblies are configured to protect a threaded sleeve of an anchor from damage due to over-insertion. An internal spring permits axial retraction of an outer shaft coupled to the sleeve independent of the inner shaft and the handle. Connection members extending along the spring create an axial stop between a drive housing and a center housing of the driver assembly. The drive housing is allowed to travel proximally in response to axial loading against the spring, while travel distally is limited by the engagement between the connection members and receivers on the center housing.

16 Claims, 12 Drawing Sheets

AXIALLY-COMPLAINT DRIVER ASSEMBLY

TECHNICAL FIELD

The present disclosure relates generally to surgical anchor drivers and, more particularly, to a driver assembly for preventing over-insertion of an anchor into bone.

BACKGROUND

Arthroscopic procedures often require soft tissue to be reattached to bone. To achieve this, anchors are typically placed in the bone and sutures attached to the anchor are passed through the tissue to securely retain the tissue in place. Typical anchors may be pound-in or screw-in type anchors, or combinations of both. However, a combination pound-in/screw-in type anchor can fail during insertion if the threaded, screw-in portion of the anchor is over-inserted by the driver assembly. Furthermore, while some contact between the threads of the anchor and the bone surface is necessary to screw the anchor into the bone, too much axial force can damage the threads, impairing the overall function of the anchor.

Some current driver assemblies, in attempting to control anchor over-insertion, rely on visual markers. These visual markers typically include laser marks on the distal end of the anchor and/or driver. However, these visual markers cannot protect the anchor from damage if they are not clearly visible, or are disregarded by the user. Driver assemblies with internal springs have also been developed to provide axial compliance of the inserter shaft to protect the anchor from over-insertion. However, with higher spring loads, friction between the knob which advances the threaded portion of the anchor and the handle grip may cause the knob to be difficult to turn.

SUMMARY

Described herein is a driver assembly which is configured to protect a threaded sleeve of an anchor from damage due to over-insertion. An internal spring permits axial retraction of the outer shaft, which is coupled to the anchor sleeve, independent of the inner shaft and the handle. Connection members extending along the spring create an axial stop between a drive housing and a center housing of the driver assembly such that the drive housing is allowed to travel proximally in response to axial loading against the spring, while travel distally is limited by the engagement between the connection members and receivers on the center housing. Advantageously, the axial compliance reaction force is internal to the driver assembly, so that rotation of the outer knob is not affected by friction.

Further examples of the driver assembly of this disclosure may include one or more of the following, in any suitable combination.

In examples, the driver assembly of this disclosure includes an outer shaft having a proximal end and a distal end. The proximal end of the outer shaft is coupled to an outer shaft hub. A drive housing is also coupled to the outer shaft hub and is also at least partially receivable within an opening in a center housing and longitudinally slidable relative to the center housing. The drive housing has a plurality of proximally-extending connection members engageable with a plurality of corresponding receivers on the center housing. A spring is at least partially disposed between the center housing and the drive housing. The drive housing is configured to travel proximally relative to the center housing in response to axial loading against the spring, while distal travel of the drive housing relative to the center housing is limited by the engagement between the connection members and the receivers. In examples, the distal end of the outer shaft is configured to engage a threaded member.

Further examples of the driver assembly include an inner shaft disposed within a cannulation of the outer shaft and axially slidable relative to the outer shaft. A proximal end of the inner shaft is coupled to the drive housing, and a distal end of the inner shaft is configured to engage a tip structure. In examples, the driver assembly also includes an actuating knob operatively coupled to the inner shaft for moving the inner shaft relative to the outer shaft. In examples, the knob includes a rounded proximal surface. The driver assembly also includes a sleeve advancement member operatively coupled to the outer shaft for moving the outer shaft relative to the inner shaft. In examples, the driver assembly includes a handle grip. At least a portion of the sleeve advancement member and the center housing is disposed within the handle grip. In examples, the handle grip includes a single cleat protruding from the handle grip for managing suture during installation of a tip structure and a threaded member into bone.

In yet further examples, a distal end of the driving housing defines internal threads which are counter-threaded to threads on a surface of the outer shaft hub. The center housing comprises a proximal portion and a distal portion, the distal portion defining the plurality of receivers. In examples, an outer diameter of the center housing is selected to be larger than an outer diameter of the proximal portion of the center housing. A proximal end of the drive housing defines an opening bordered by a plurality of support members extending between the plurality of connection members. The support members are configured to support the spring. In examples, the connection members are defined by an elongated member terminating in a radially-extending foot. In examples, the receivers are in the form of apertures defined by an annular surface of the distal portion of the center housing. In examples, the spring is a compression spring.

Alternative examples of the driver assembly of this disclosure include a handle grip having a proximal end, a distal end and a longitudinal axis extending therebetween. An outer shaft has an open cannulation extending from a proximal end to a distal end. The proximal end of the outer shaft is coupled to an outer shaft hub disposed within the handle grip such that the outer shaft extends from the distal end of the handle grip. An inner shaft is disposed within the outer shaft cannulation and moveable along the longitudinal axis relative to the outer shaft. A proximal end of the inner shaft is operatively coupled to a suture capture knob positioned proximally to the handle grip. A sleeve advancement member is disposed near a proximal end of the handle grip, and a linking mechanism rotationally couples the sleeve advancement member and the outer shaft hub. Rotation of the sleeve advancement member causes the outer shaft to move axially relative to the inner shaft. In further examples, the linking mechanism includes a rod having a first linkage at a proximal end and a second linkage at a distal end. The first linkage is rotationally coupled to the sleeve advancement member and the second linkage rotationally coupled to the outer shaft hub. In other examples, the linking mechanism includes a gear having a first set of teeth for engaging a second set of teeth on the sleeve advancement member and a third set of teeth on the outer shaft hub. In examples, a distal end of the handle grip includes a stationary cap for enclosing the handle grip.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein.

DETAILED DESCRIPTION

In the description that follows, like components have been given the same reference numerals, regardless of whether they are shown in different examples. To illustrate example (s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used to represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts.

Figure 1:
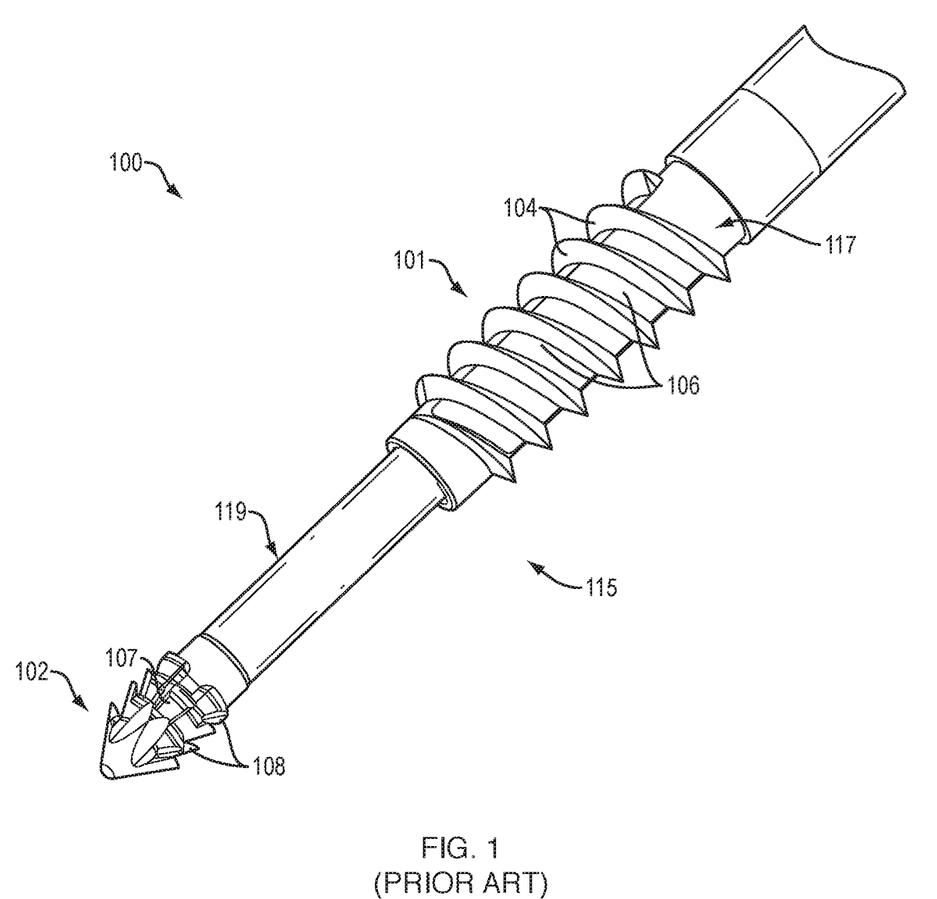
FIG. 1 is an illustration of a prior art anchor/driver assembly.

FIG. 1 shows a prior art anchor/driver assembly 100 for securing a tissue to bone. The assembly 100 generally includes a threaded anchor sleeve 101 and a tip structure 102. In examples, the sleeve 101 includes at least one open helical coil 104 having a plurality of open spacing sections 106 between turns of the open helical coil 104 for allowing bony ingrowth from the bone into an internal volume defined within the open helical coil 104. In examples, the tip structure 102 includes a suture capture member, such as a plug (not shown), advanceable through an internal cavity of the tip structure 102 to lock one or more sutures in an eyelet 107 extending through the tip structure 102. The tip structure 102 can terminate in a pointed and/or barbed tip for breaking through bone during insertion, or can be rounded or flattened for various examples where pre-drilling of the bone obviates the need for a distal, terminal point. The tip structure may also include barbs 108 protruding therefrom to improve pullout strength of the tip structure 102.

The assembly 100 can be installed, for example, into a bone using an anchor driver 115. The anchor driver 115 generally includes an outer shaft 117 insertable into the sleeve 101. In examples, the outer shaft 117 may be grooved to engage longitudinal runners (not shown) extending through the internal volume of the sleeve 101. In some examples, the tip structure 102 is pounded into the bone and the sleeve 101 is screwed or otherwise advanced by the outer shaft 117 into the bone over the tip structure 102 to securely lock the tip structure 102 into the bone. An inner shaft (not shown) is then actuated to advance the plug into engagement with the suture within the eyelet 107 of the tip structure 102. Additional non-limiting examples of the anchor/driver assembly 100 can be found in U.S. Pat. No. 9,526,488, to Smith & Nephew, Inc. (Memphis, Tenn.), the entire contents of which are incorporated herein by reference.

Figure 2A:
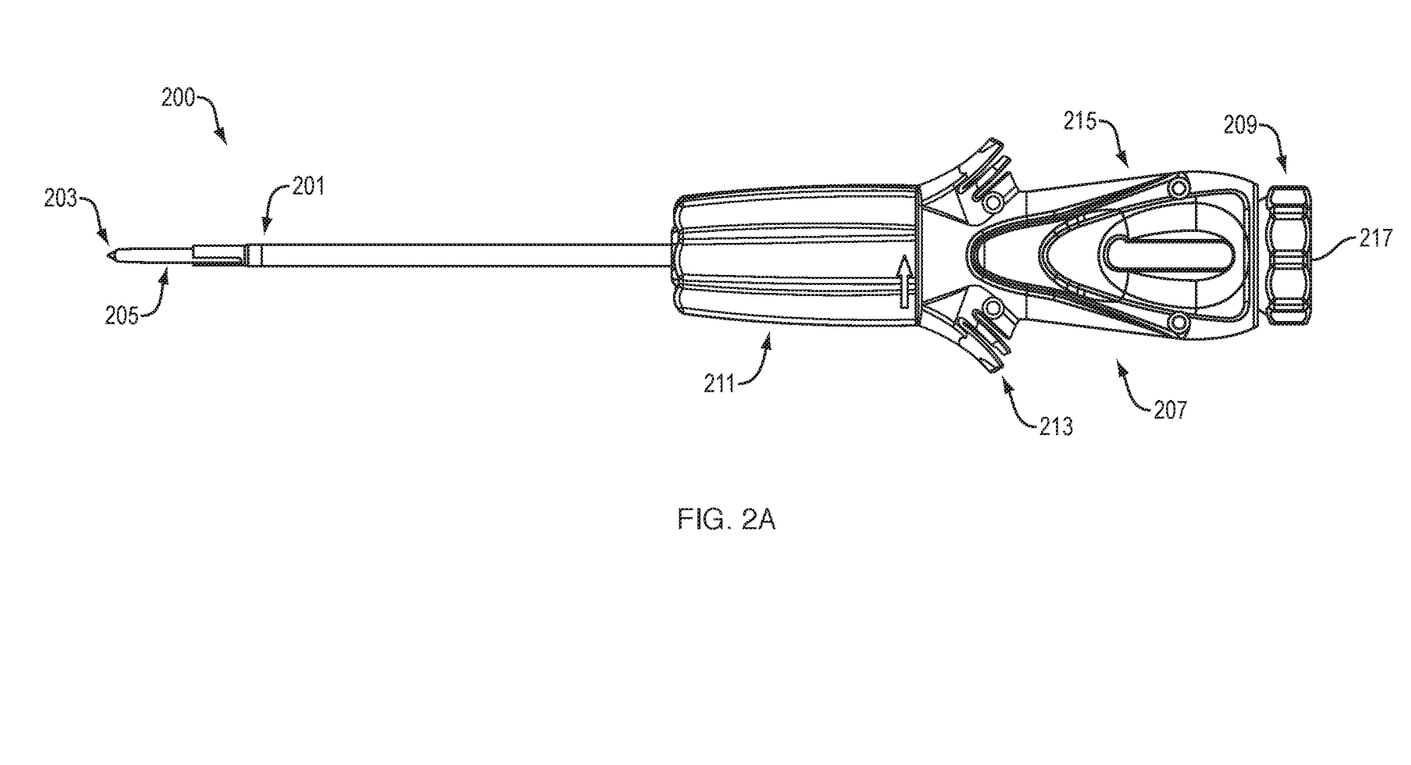
FIGS. 2A-E illustrate the component parts of an example of a driver assembly of this disclosure.

Turning now to FIG. 2A, an example of a driver assembly 200 of this disclosure is shown in a side view. The driver assembly 200 may be used to insert a sleeve, such as sleeve 101, and a tip structure, such as tip structure 102, into bone. Additionally, the driver assembly 200 could be used with any combination device in which the pound-in and screw-in subassemblies can be mechanically decoupled, including devices with guides. The driver assembly 200 could also be used with combination devices in which the pound-in and screw-in phases do not appear to be readily decoupled. Advantageously, the driver assembly 200 of this disclosure is configured such that impact or other axial forces applied to the sleeve while pounding in the tip structure can be alleviated to prevent over-insertion damage, as described in more detail below.

As shown in FIG. 2A, the driver assembly 200 includes an outer shaft 201 for engaging with the sleeve or other threaded structure, an inner shaft 203 extending through the outer shaft 201 for engaging with a tip structure, and a handle assembly 207 for holding and operating the driver assembly 200. In various examples, the driver assembly 200 can also include one or more intermediate shafts 205 to, for example, provide additional stiffness when pounding in a tip structure. The handle assembly 207 can include a suture capture knob 209 for advancing a suture capture member to capture a suture, a sleeve advancement member 211 for screwing in a sleeve, and a handle grip 215 for holding and/or maneuvering the driver assembly 200 during insertion of the anchor into bone. The handle grip 215 can include one or more cleats 213 protruding from the handle grip 215 for placing and/or maintaining tension on a suture during installation of the sleeve and the tip structure into bone. The handle assembly 207 may also include a pounding surface 217 for pounding the tip structure into bone.

Figure 2B:
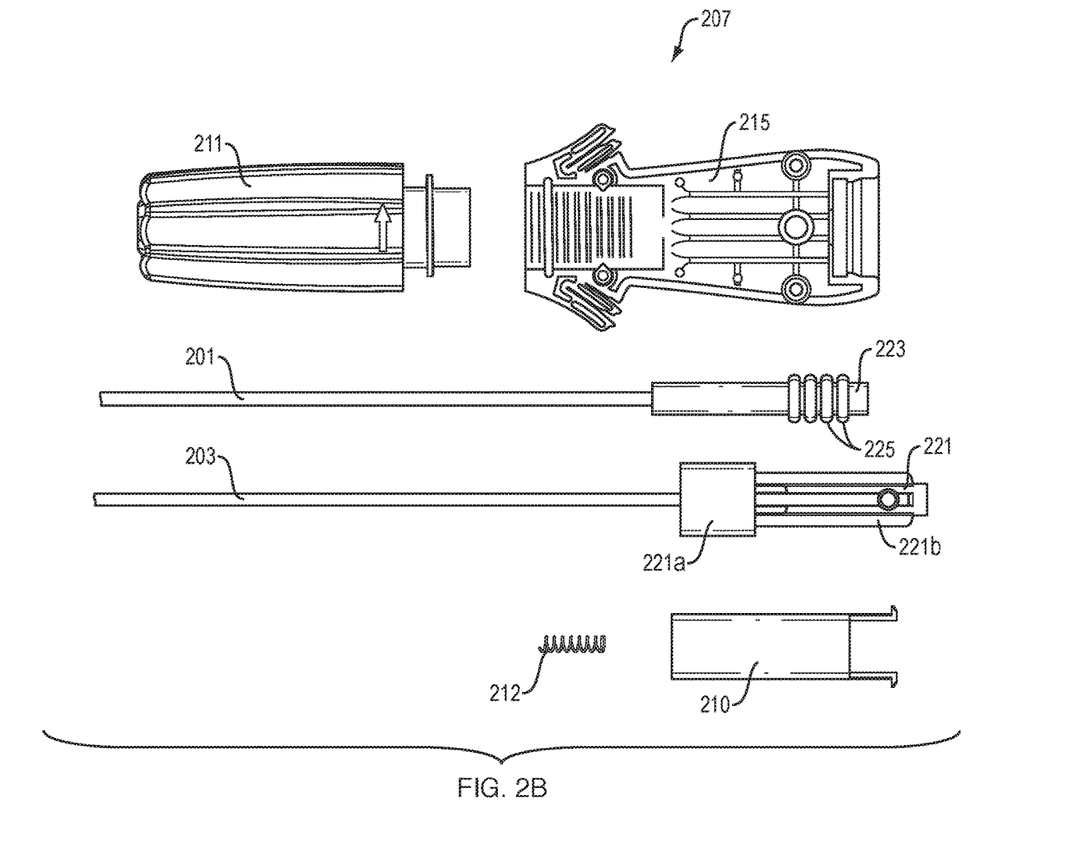

FIG. 2B shows the primary components of the handle assembly 207 of this disclosure in a disassembled view. In particular, FIG. 2B shows the sleeve advancement member 211, a cross-section of the handle grip 215, the outer shaft 201, and the inner shaft 203. A proximal end of the outer shaft 201 is coupled to an outer shaft hub 223 and a proximal end of the inner shaft 203 is coupled to a center housing 221. The center housing 221 includes a distal portion 221a having a larger outer diameter than a grooved proximal portion 221b. In examples, a drive housing 210 defines internal threads (FIG. 3B) which are counter-threaded to threads 225 on the outer shaft hub 223. The drive housing 210 is configured to engage both the sleeve advancement member 211 and the outer shaft hub 223 such that twisting or rotating the sleeve advancement member 211 rotates the outer shaft hub 223. This causes the outer shaft hub 223 to advance distally relative to the center housing 221, consequently advancing the outer shaft 201 relative to the inner shaft 203. This movement in turn causes the sleeve to advance into engagement with the tip structure. The handle assembly 207 also includes a spring 212, the purpose of which will be described in more detail below.

Figure 2C:
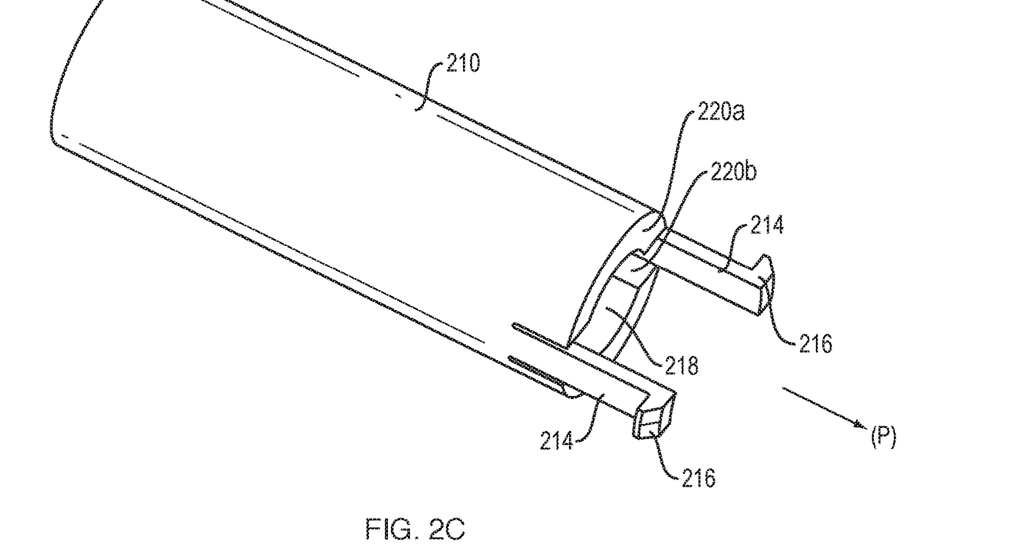

Turning now to FIG. 2C, the drive housing 210 includes a plurality of connection members 214 extending in the proximal direction (P) from a proximal end the drive housing 210. The connection members 214 are part of a mechanism configured to constrain the distal motion of the drive housing 210 with respect to the center housing 221 such that the drive housing 210 and the center housing 221 are not pushed apart by a spring force, while still allowing proximal movement of the drive housing 210 relative to the center housing 221. In FIG. 2C, the connection members 214 are shown in the form of elongated flexures. However, it is contemplated that other types of connection members (such as pins) could be used. Furthermore, while two connection members 214 are shown in FIG. 2C, it will be appreciated that more or fewer than two connection members 214 may be used. In the example of FIG. 2C, each of the connection members 214 terminates in a radially-extending foot 216. The proximal end of the drive housing 210 further defines an opening 218 bordered by semi-circular support members 220a, 220b extending between the connection members 214 for supporting the spring 212.

Figure 2D:
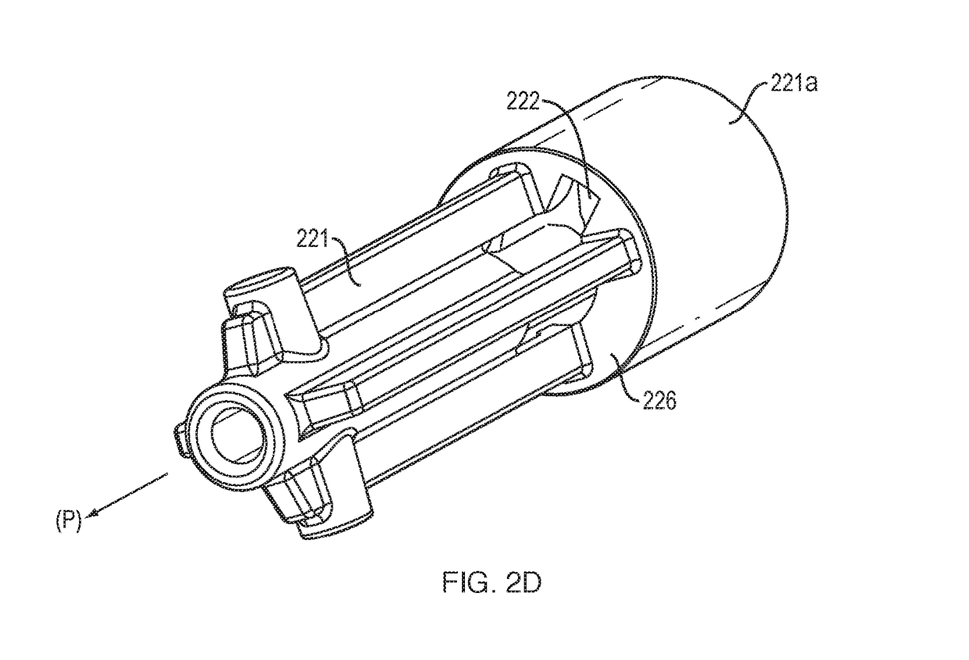
Figure 2E:
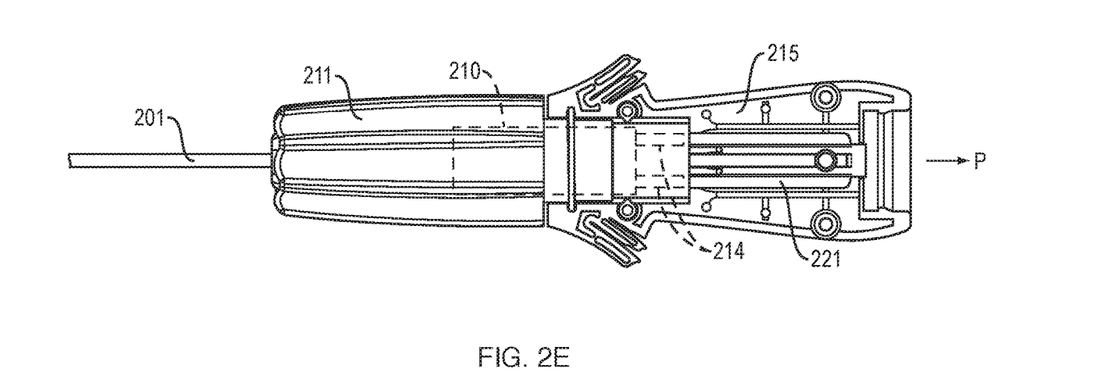

In FIG. 2D, it can be seen that the distal end 221a of the center housing 221 includes a proximally-facing annular surface 226. The annular surface 226 defines a plurality of receivers 222 for engaging the corresponding connection members 214 of the drive housing 210 to limit distal motion of the drive housing 210 relative to the center housing 221. In FIG. 2D, the receivers 222 are shown in the form of apertures configured to engage the feet 216 of the connection members 214, as further described below. However, it should be appreciated that other types of receivers, such as slots, could be used. FIG. 2E illustrates the outer shaft 201, the sleeve advancement member 211, the center housing 221, and the handle grip 215 in an assembled view, with the relative position of the drive housing 210 and connection members 214 indicated.

In various examples, the handle grip 215, the sleeve advancement member 211, the center housing 221, the outer shaft hub 223 and/or the drive housing 210 can each be manufactured from a polymer material and via an injection molding process. However, any other suitable material (e.g., metals, composites, wood) and/or process (e.g., extrusion, machining, electro-chemical machining) can be used. The handle grip 215, the center housing 221, the sleeve advancement member 211, and/or the drive housing 210 can be coupled via an interference fit. However, any other suitable method of coupling (e.g., screws, adhesives, rivets) can be used. The components of the outer shaft 201, the inner shaft 203, and/or the intermediate shaft(s) 205 can be made from a metal material via an extrusion or drawing process. However, any other suitable material (e.g., plastics, composites) and/or process (e.g., injection molding, casting, machining, electro-chemical machining) can be used. The components of the outer shaft 201, the inner shaft 203, and/or the intermediate shaft(s) 205 can be coupled to the handle grip 215, the outer drive hub 223, the center housing 221 and/or the sleeve advancement member 211 via an interference fit. However, any other suitable method of coupling (e.g., screws, adhesives, rivets) can be used.

Figure 3A:
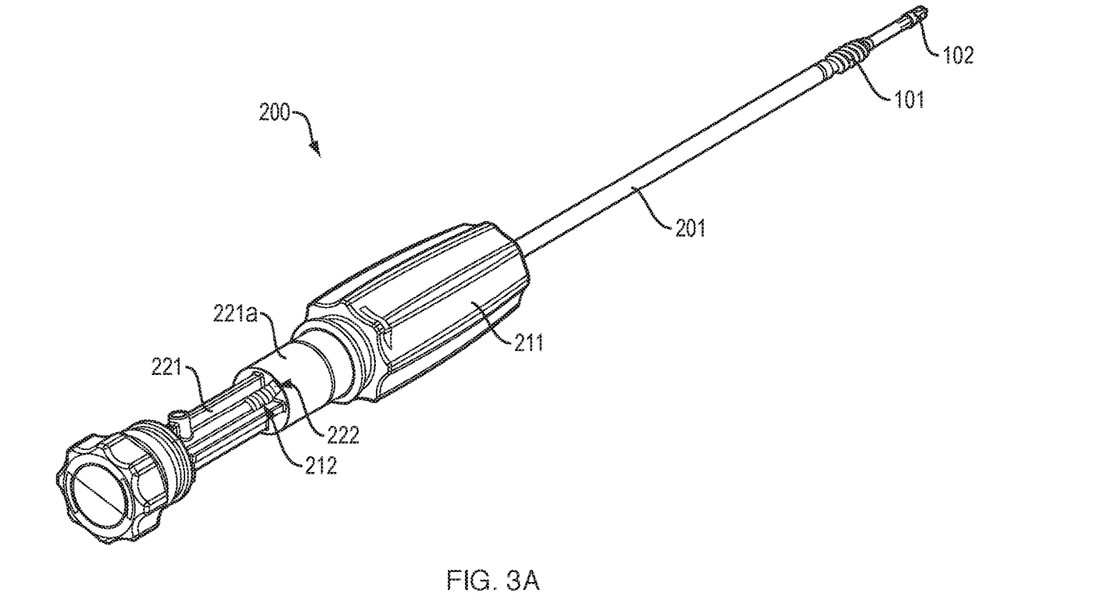
FIGS. 3A-D illustrate the use of the driver assembly of this disclosure.
Figure 3B:
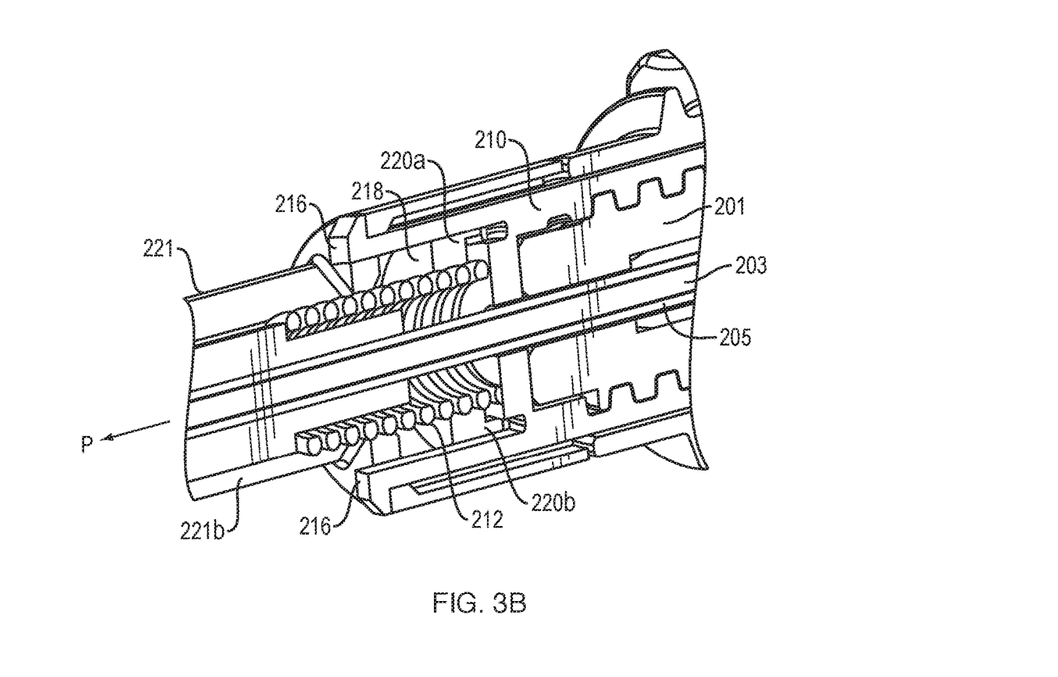
Figure 3C:
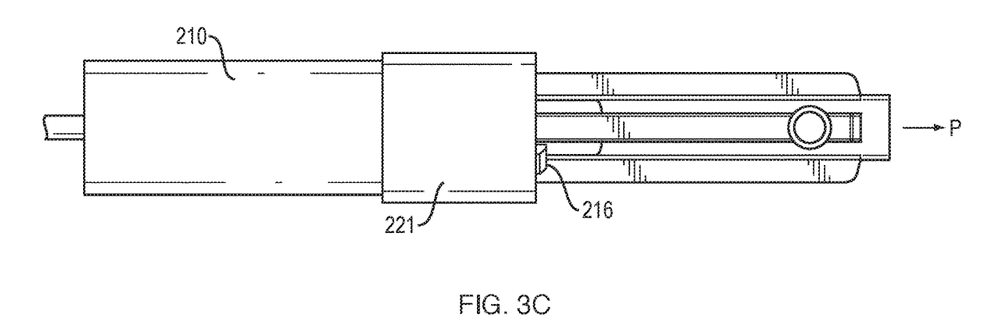
Figure 3D:
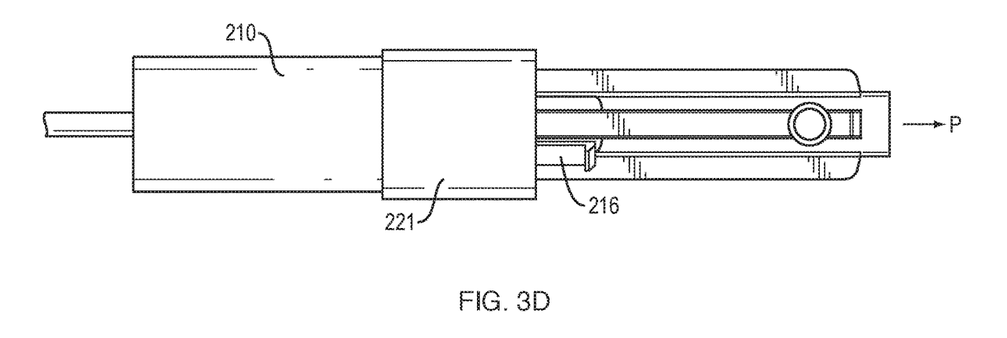

Turning now to FIG. 3A, in use, various examples of the driver assembly 200 of this disclosure can alleviate impact forces on the sleeve 101 by including the spring 212 within the center housing 221. The spring 212 is configured to allow a relative motion between the outer shaft 201 and the inner shaft 203 (FIG. 3B), thereby absorbing at least a portion of the impact forces exerted on the sleeve 101 during the pounding-in of the tip structure 102. As shown in more detail in FIG. 3B, the spring 212 can be positioned between the support members 220a, 220b within the opening 218 of the drive housing 210 such that the spring 212 extends into the proximal portion 221b of the center housing 221 and around the inner shaft 203 (and any intermediate shafts 205). It will be appreciated that, while the spring 212 is depicted to be a compression spring, any suitable spring 212 can be used. Additionally, it is contemplated that any means of introducing compliance between the drive housing 210 and the center housing 221 (for example, foam, rubber, magnet pairs, trapped fluid, flexures, etc.), could be used instead of the spring 212. Thus, upon an impact or other axial force being applied to the sleeve 101, the outer shaft 201 is configured to move proximally in the direction (P) relative to inner shaft 203. This relative proximal motion of the outer shaft 201 moves the drive housing 210 through the center housing 221 from an initial, first position (FIG. 3C) to an axially-compliant, second position (FIG. 3D), thereby compressing or otherwise actuating the spring 212 and absorbing or otherwise relieving the impact forces. As the drive housing 210 moves proximally through the center housing 221, the receivers 222 in the center housing 221 allow the connection members 214 to travel proximally in response to axial loading against the spring 212. At the same time, travel distally by the drive housing 210 relative to the center housing 221 is limited by engagement of the feet 216 with the receivers 220 in the center housing 221. Thus, the connection members 214 create an axial stop between the drive housing 210 and the center housing 221 to counteract the friction loading that causes the sleeve advancement member 211 to be hard to turn.

Figure 4A:
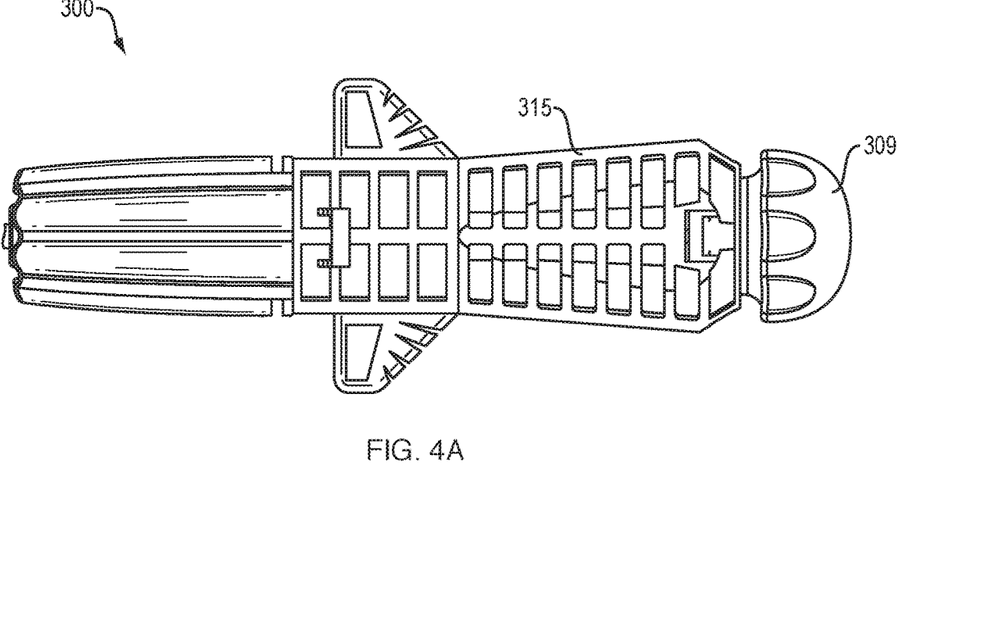
FIGS. 4A and 4B show alternative examples of the suture capture knob of this disclosure.
Figure 4B:
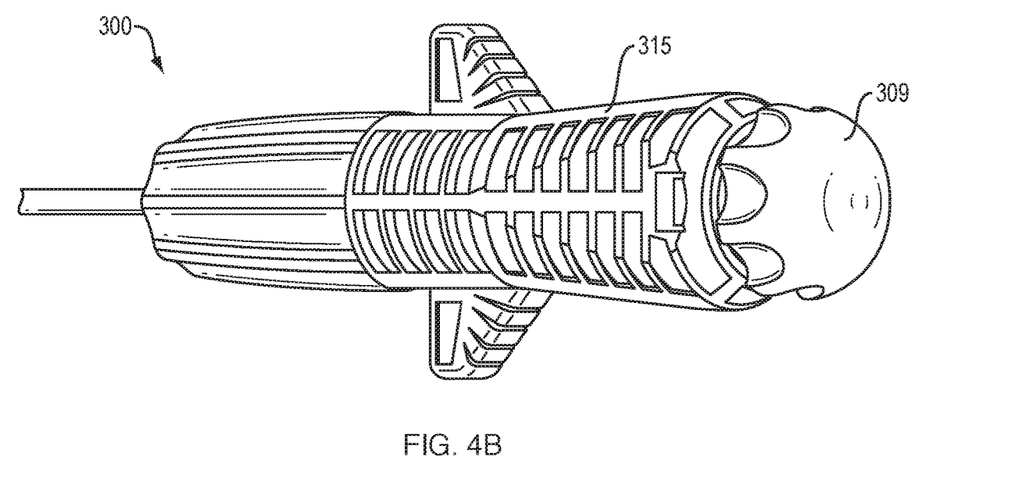

Variations of the suture capture knob 209 will now be discussed with reference to FIGS. 4A and 4B. In FIG. 2A, for example, the suture capture knob 209 is shown as having a flat proximal terminus with an abrupt edge transition toward the pounding surface 217. When the user applies the moderate downward pressure required to use the driver assembly 200, the suture capture knob 209 can press uncomfortably on the palm of the hand. Therefore, it some applications, it may be more convenient to have a suture capture knob 209 with a rounded proximal surface. As shown in FIGS. 4A and 4B, the suture capture knob 309 is rounded proximally and abrupt transitions (i.e., corners) have been eliminated to advantageously make the driver assembly 300 fit more comfortably in the user's hand. In addition, a maximum diameter of the knob 309 is larger than the maximum diameter of the knob 209 to create a smoother transition to the handle grip 315. Thus, the driver assembly 300 is more comfortable for the user when applying moderate downward pressure on the driver assembly 300, which facilitates the threading of the sleeve 101 into bone.

Figure 5A:
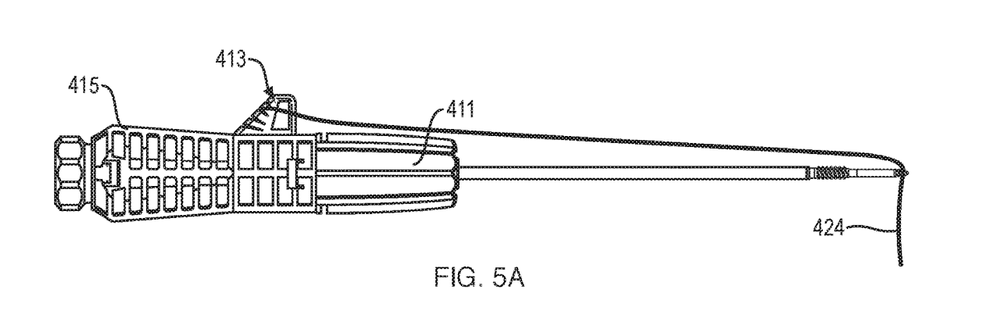
FIGS. 5A-D show alternative examples of the handle grip of this disclosure.
Figure 5B:
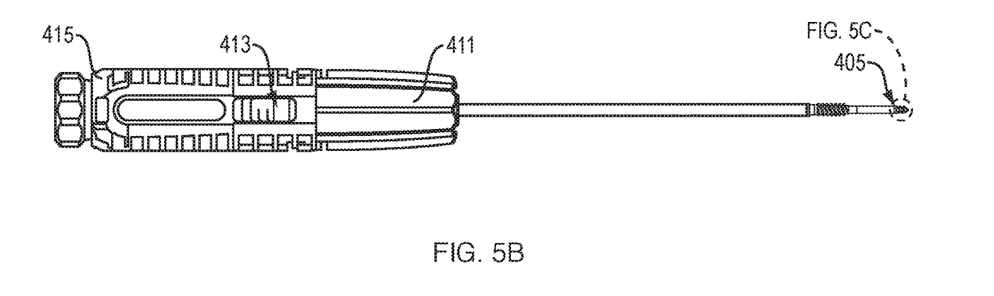
Figure 5C:
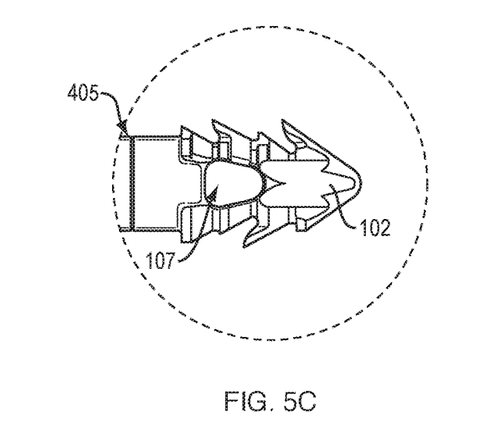
Figure 5D:
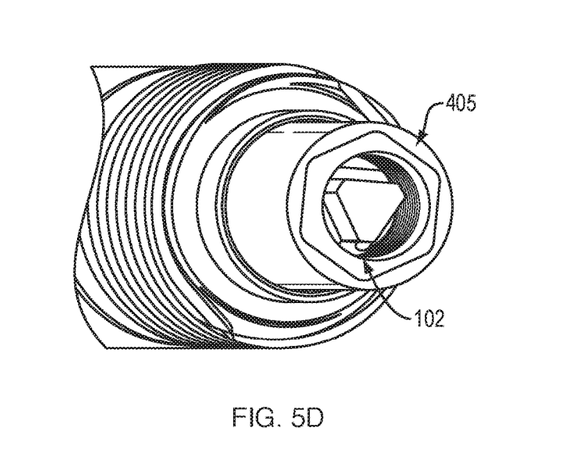

Variations of the handle grip 215 will now be discussed with reference to FIGS. 5A-C. In FIG. 2A, for example, the handle grip 215 is shown as including a pair of symmetrical cleats 213 protruding from the handle grip 215 for placing and/or maintaining tension on a suture during installation of the sleeve 101 and the tip structure 102 into bone. However, in some applications, it may be more convenient to have only one cleat 213 protruding from the handle grip for ease of suture management. As shown in FIGS. 5A and 5B, the handle grip 415 includes a single cleat 413 which is preferentially aligned with a fixed orientation of the eyelet 107 of the tip structure 102 such that suture 424 passed through the eyelet 107 naturally aligns to the single cleat 413. This orientation of the tip structure 102 to the handle grip 415 is controlled by the mating interface between the tip structure 102 and the intermediate shaft 405 (FIG. 5C). For example, the mating interface may include a polygonal mating surface which limits the rotation of the tip structure 102 relative to the intermediate shaft 405, as in FIG. 5C. However, other mating interfaces which limits the rotation of the tip structure 102 relative to the intermediate shaft 405 are contemplated by this disclosure. Advantageously, in addition to simplifying management of the suture 424, having a single cleat 413 allows the sleeve advancement member 411 to be less obscured by the suture 424 and therefore more easily rotated by the user.

Figure 6A:
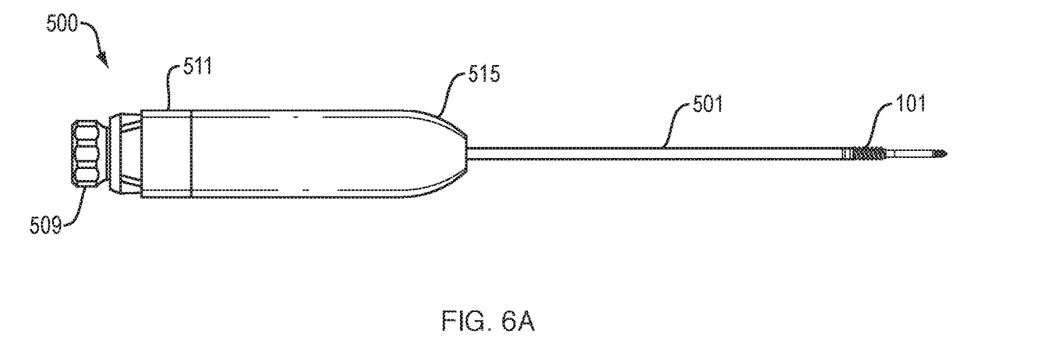
FIGS. 6A-C illustrate an alternative example of the driver assembly of this disclosure.
Figure 6B:
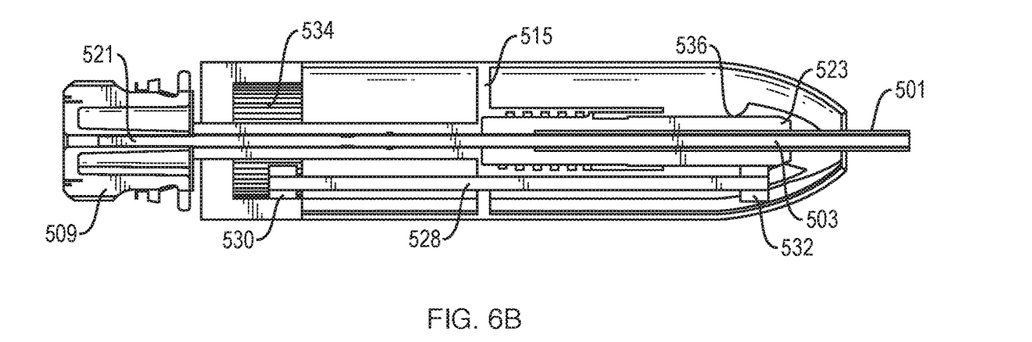
Figure 6C:
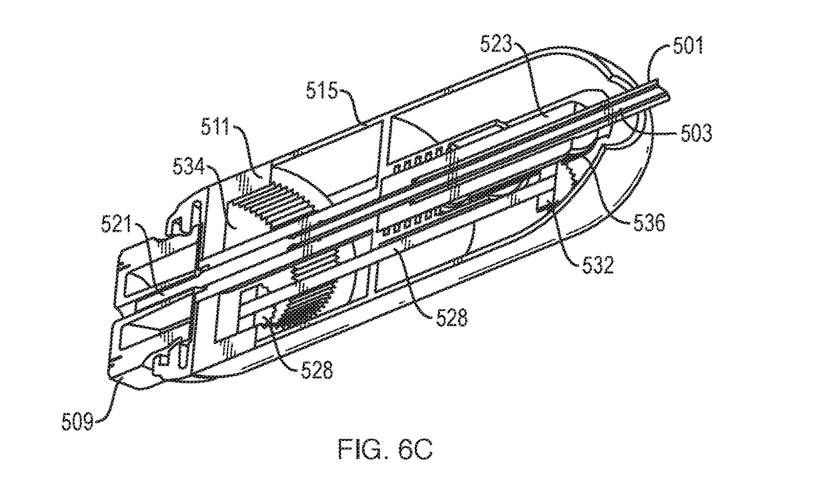

Variations on the driver assembly 200 will now be discussed with regard to FIGS. 6A-C. In FIG. 2A, for example, the sleeve advancement member 211 is shown as being located at a distal end of the handle grip 215. However, in some applications, it may be more convenient to have the sleeve advancement member 211 located closer to the suture capture knob 209 (i.e., towards a proximal end of the handle grip 215) for ease of use. FIG. 6A illustrates an example of a driver assembly 500 in which the sleeve advancement member 511 is located near the suture capture knob 509 towards a proximal end of the handle grip 515. As shown in FIG. 6A, the outer shaft 501 extends from the distal end of the handle grip 515 for engaging the sleeve 101. As illustrated in more detail in FIGS. 6B and 6C, a proximal end of the outer shaft 501 is coupled to an outer shaft hub 523 disposed within the handle grip 515. The inner shaft 503 is axially slidable within a cannulation of the outer shaft 501 relative to the outer shaft 501. A proximal end of the inner shaft 503 is coupled a center housing 521 which is operatively coupled to the suture capture knob 509 positioned proximally to the handle grip 515. As described above, the sleeve advancement member 511 is disposed between the handle grip 515 and the suture capture knob 509.

In order to operatively couple the outer shaft hub 523 (and thus, the outer shaft 501) with the sleeve advancement member 511, a linking mechanism is used to engage the outer shaft hub 523 and the sleeve advancement member 511. In examples, the linking mechanism includes a rod 528 having a first linkage 530 (for example, a first gear) at a proximal end of the rod 528 and a second linkage 532 (for example, a second gear) at a distal end of the rod 528. The first linkage 530 engages a gear 534 which is rotationally coupled to the sleeve advancement member 511, while the second linkage 532 engages a spline 536 on the outer shaft hub 523. Thus, rotation of the sleeve advancement member 511 causes rotation of the outer shaft hub 523, which in turn causes the outer shaft 501 to move axially relative to the inner shaft 503. Notably, while the linking mechanism is shown in FIGS. 6B and 6C as including gears, other rotational linkages, such as bands, belts, or chains, are contemplated by this disclosure.

Figure 7A:
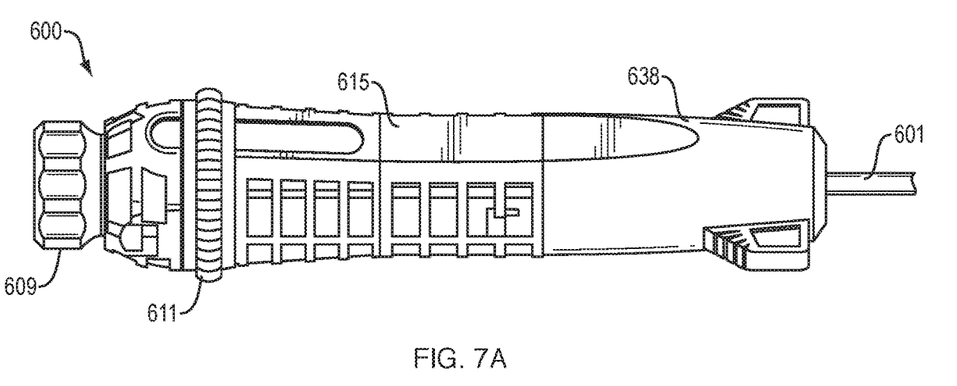
FIGS. 7A-C illustrate an alternative example of the driver assembly of FIGS. 6A-C.
Figure 7B:
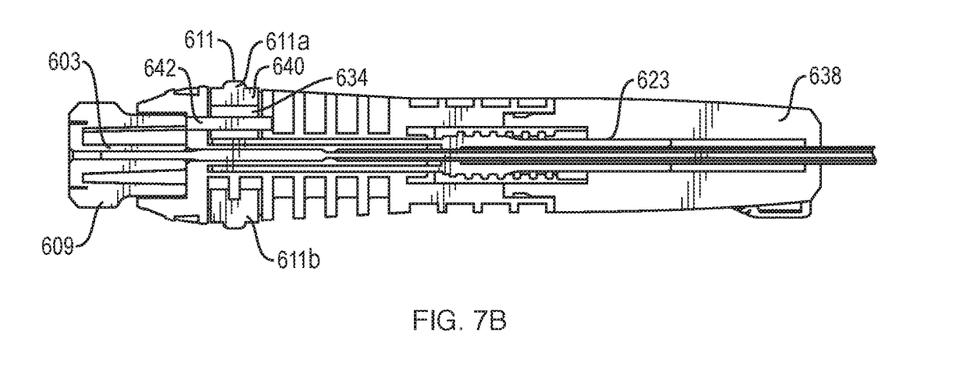
Figure 7C:
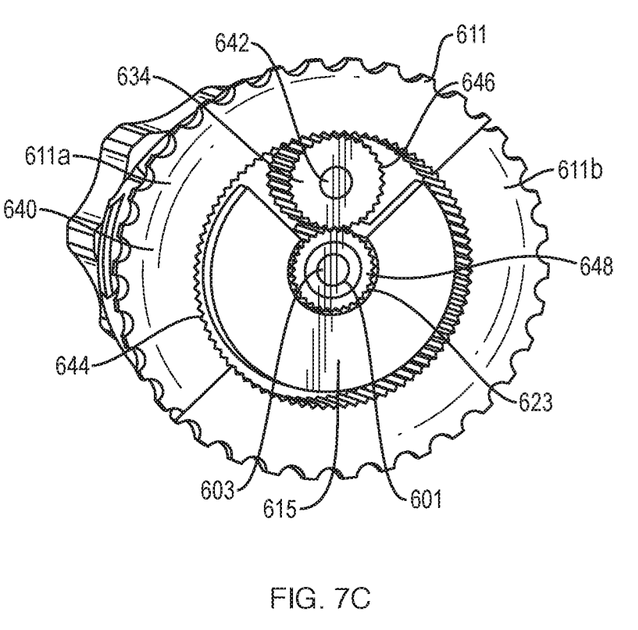

Another variation on the driver assembly 500 will now be discussed with regard to FIGS. 7A-C. FIG. 7A illustrates an alternative example of the driver assembly 600 in which the sleeve advancement member 611 is located near the suture capture knob 609 towards a proximal end of the handle grip 615. As shown in FIG. 7A, a distal end of the handle grip 615 includes a stationary cap 638 for enclosing the handle grip 615. The outer shaft 601 extends from the stationary cap 638 for engaging the sleeve 101. As shown in more detail in FIG. 7B, the sleeve advancement member 611 defines an internal ring gear 640. In examples, the sleeve advancement member 611 is fabricated in two pieces 611a, 611b to facilitate its assembly onto the handle grip 615. An idler gear 634 is mounted on a rod or shaft 642 within the handle grip 615. As shown in FIG. 7C, the internal ring gear 640 includes gear teeth 644 that mate with gear teeth 646 on the idler gear 634 which, in turn, mate with gear teeth or splines 648 on an exterior of the outer shaft hub 623. Thus, rotation of the sleeve advancement member 611 causes rotation of the outer shaft hub 623, which in turn causes the outer shaft 601 to move axially relative to the inner shaft 603 to install the sleeve 101. Notably, while the linking mechanism is shown in FIGS. 7B and 7C as including gears, other rotational linkages, such as bands, belts, or chains, are contemplated by this disclosure.

While the disclosure has been particularly shown and described with references to preferred examples thereof, it will be understood by those skilled in the art that various changes in form and details may be made therein without departing from the spirit and scope of the present application as defined by the appended claims. Such variations are intended to be covered by the scope of this present application. As such, the foregoing description of examples of the present application is not intended to be limiting, the full scope rather being conveyed by the appended claims.

What is claimed is:

1. A driver assembly comprising:
an outer shaft having a proximal end and a distal end, the proximal end of the outer shaft coupled to an outer shaft hub;
a drive housing coupled to the outer shaft hub, the drive housing at least partially receivable within an opening in a center housing and longitudinally slidable relative to the center housing, the drive housing having a plurality of proximally-extending connection members engageable with a plurality of corresponding receivers on the center housing; and
a spring at least partially disposed between the center housing and the drive housing;
wherein the drive housing is configured to travel proximally relative to the center housing in response to axial loading against the spring, while distal travel of the drive housing relative to the center housing is limited by the engagement between the connection members and the receivers.

2. The assembly of claim 1, wherein the distal end of the outer shaft is configured to engage a threaded member.

3. The assembly of claim 1, further comprising an inner shaft disposed within a cannulation of the outer shaft and axially slidable relative to the outer shaft.

4. The assembly of claim 3, wherein a proximal end of the inner shaft is coupled to the drive housing.

5. The assembly of claim 3, wherein a distal end of the inner shaft is configured to engage a tip structure.

6. The assembly of claim 3, further comprising an actuating knob operatively coupled to the inner shaft for moving the inner shaft relative to the outer shaft, the knob comprising a rounded proximal surface.

7. The assembly of claim 3, further comprising a sleeve advancement member operatively coupled to the outer shaft for moving the outer shaft relative to the inner shaft.

8. The assembly of claim 7, further comprising a handle grip, at least a portion of the sleeve advancement member and the center housing disposed within the handle grip.

9. The assembly of claim 8, wherein the handle grip includes a single cleat protruding from the handle grip for managing suture during installation of a tip structure and a threaded member into bone.

10. The assembly of claim 1, wherein a distal end of the driving housing defines internal threads which are counter-threaded to threads on a surface of the outer shaft hub.

11. The assembly of claim 1, wherein the center housing comprises a proximal portion and a distal portion, the distal portion defining the plurality of receivers.

12. The assembly of claim 11, wherein an outer diameter of the distal portion of the center housing is selected to be larger than an outer diameter of the proximal portion of the center housing.

13. The assembly of claim 1, wherein a proximal end of the drive housing defines an opening bordered by a plurality of support members extending between the plurality of connection members, the support members configured to support the spring.

14. The assembly of claim 1, wherein the connection members are defined by an elongated member terminating in a radially-extending foot.

15. The assembly of claim 1, wherein the receivers are in the form of apertures defined by an annular surface of the distal portion of the center housing.

16. The assembly of claim 1, wherein the spring is a compression spring.

* * * * *